(12) United States Patent
Nishimoto et al.

(10) Patent No.: US 8,524,889 B2
(45) Date of Patent: Sep. 3, 2013

(54) HIGHLY-BRANCHED STARCH, ITS PRODUCTION AND USES

(75) Inventors: Tomoyuki Nishimoto, Okayama (JP); Katsuhiko Hino, Okayama (JP); Takanori Okura, Okayama (JP); Hiroto Chaen, Okayama (JP); Shigeharu Fukuda, Okayama (JP); Toshio Miyake, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 0 days.

(21) Appl. No.: 13/443,296

(22) Filed: Apr. 10, 2012

(65) Prior Publication Data

US 2012/0196331 A1 Aug. 2, 2012

Related U.S. Application Data

(62) Division of application No. 11/911,090, filed as application No. PCT/JP2006/304962 on Mar. 14, 2006, now Pat. No. 8,168,778.

(30) Foreign Application Priority Data

Apr. 8, 2005 (JP) ................................. 2005-111780
Oct. 13, 2005 (JP) ................................. 2005-298253

(51) Int. Cl.
*C07H 1/06* (2006.01)
*C08B 31/00* (2006.01)

(52) U.S. Cl.
USPC ............................ 536/127; 536/124; 536/102

(58) Field of Classification Search
USPC ......................................... 536/127, 124, 102
See application file for complete search history.

(56) References Cited

U.S. PATENT DOCUMENTS

| | | | |
|---|---|---|---|
| 6,248,566 B1 | 6/2001 | Imanaka et al. | |
| 8,168,778 B2 * | 5/2012 | Nishimoto et al. | 536/102 |
| 2002/0012973 A1 * | 1/2002 | Antrim et al. | 435/100 |
| 2004/0014961 A1 | 1/2004 | Backer et al. | |
| 2007/0066565 A1 | 3/2007 | Mukai et al. | |

FOREIGN PATENT DOCUMENTS

| | | |
|---|---|---|
| AU | 200043052 B2 | 4/2000 |
| EP | 0710674 A2 | 5/1996 |
| EP | 1369432 A2 | 12/2003 |
| JP | 134104 A | 5/1996 |
| JP | 8134104 A | 5/1996 |
| JP | 294601 A | 10/2001 |
| JP | 2001294601 A | 10/2001 |
| JP | 200278497 A | 3/2002 |
| WO | 0066633 A1 | 11/2000 |
| WO | 2005021564 A1 | 3/2005 |

OTHER PUBLICATIONS

Andre et al., Docking exploration of alpha-(1,6) branched maltodextrins in barley alpha-amylase, Recent Advances in Enzymes in Grain Processes, pp. 9-14 (Jan. 1, 2003).

* cited by examiner

*Primary Examiner* — Patrick Lewis
*Assistant Examiner* — Everett White
(74) *Attorney, Agent, or Firm* — Browdy and Neimark, PLLC

(57) ABSTRACT

An object of the present invention is to provide a novel starchy substance having a retrogradation-resistance, a process for producing the starchy substance efficiently from a material starch by enzymatic reaction, and uses thereof. The present invention attains the above object by providing branched starch having 6-α-maltosyl- and/or 6-α-maltotetraosyl-structure(s) with a marked retrogradation-resistance, a process for producing the branched starch without lowering the molecular weight of material starch, and uses thereof.

2 Claims, 3 Drawing Sheets

HIGHLY-BRANCHED STARCH, ITS PRODUCTION AND USES

CROSS-REFERENCE TO RELATED APPLICATIONS

The present application is a divisional of application Ser. No. 11/911,090, filed Oct. 9, 2007, now U.S. Pat. No. 8,168,778 which is a 371 national stage application of PCT/JP2006/304962, filed Mar. 14, 2006, which claims priority of Japanese application no. 2005-111780, filed Apr. 8, 2005 and Japanese application no. 2005-298253, filed Oct. 13, 2005.

TECHNICAL FIELD

The present invention relates to branched starch, its preparation and uses. More particularly, the present invention relates to branched starch having 6-α-maltosyl- and/or 6-α-maltotetraosyl-branched structure(s), its preparation and uses.

BACKGROUND ART

Starch, which is a mixture of amylose and amylopectin, is a glucan stored in cells of seed or rhizome of higher plants. Amylose is a α-1,4-glucan in which glucoses are linearly bound by α-1,4-glucosidic linkage. Amylopectin has branched structures in which some glucoses of other α-1,4-glucan are bound to branches of α-1,4-glucans with glucose polymerization degree of generally 6 or more by α-1,6-glucosidic linkage. Water dispersion of starch was swollen by heating to be gelatinized starch, but when it is left after cooling, it tend to easily gelate by retrogradation. Gelatinized starch has been used as food by since ancient times, as a main food material with good workability, low cost, and good storage quality, and also as a thickener, water-retention agent, or colloid-stabilizing agent for improving food properties or reserving food qualities. Liquefied starch is used for an industrial material for production of glucose, isomerized sugar, maltooligosaccharides, and syrups. But gelatinized or liquefied starch have disadvantageous properties as easily gelating by retrogradation during storage resulting in unfitting for food with hardening by loss of water-retentivity and being difficult to be act on by a enzyme.

Under these circumstances, many attempts were made to give retrogradation-resistance to gelatinized starch by chemical modification, such as esterification, etherification, or oxidation of starch. But modified starch in which glucose lost its natural structure by addition of particular kind of functional groups is not commonly used because of safety concern about long-term intake of them.

A method of adding retrogradation-resistance to starch by enzymatic modifications is proposed. Japanese Patent Kokai 134104/1996 proposed a method of forming water-soluble macrocyclic glucans by allowing branching enzyme (EC 2.4.1.18), which cleave α-1,4-glucosidic linkages and form α-1,6-glucosidic linkages by transglycosilation, 4-α-glucanogransferase (D-enzyme, EC 2.4.1.25) or CGTase (EC 2.4.1.19) to act on starch liquefying solution. But because the forming of macrocyclic glucans accompanies large decrease of molecular weight of substrate resulting in low viscosity, there is a problem that the characteristics of the material liquefied starch is lost. Japanese Patent Kokai 294601/2001 proposed the method of forming highly branched starch, mainly constructed of branches with glucose polymerization degree of 4 to 7 and densely-branched compared to the material starch, using the branching enzyme from *Neurospora crassa* which hardly lower the molecular weight of the starch. But above branched starch is not yet led to industrial preparation and application because the safety of *Neurospora crassa*, an atypical fungus, is not determined. Japanese Patent Kokai 78497/2002 proposed a method of forming branched starch mainly constructed of branches with DP of glucose of 6 or 7, in which SBE-II (branching enzyme from barley) and phosphorylase are allowed to act on glucose-1-phosphate and maltoologosaccharides. But it is very difficult to industrially use SBE-II (branching enzyme from barley), phosphorylase and glucose-1-phosphate. Under above circumstances, providing a starchy substance is expected, in which properties including retrogradation property were improved with little decrease of molecular weight.

DISCLOSURE OF INVENTION

An object of the present invention is to provide a novel starchy substance having a retrogradation-resistance, a process for producing the starchy substance efficiently from material starch by enzymatic reaction, and uses thereof.

To attain the above object, the present inventors have extensively studied on the use of various glycosyl-transferring enzymes. In the course of the studies, the present inventors found that when a cyclic-maltosylmaltose-forming enzyme (hereinafter, abbreviated as "CMM-forming enzyme"), which forms a cyclic maltosylmaltose, i.e. CMM, having the structure of cyclo{→6)-α-D-glucopyranosyl-(1→4)-α-D-glucopyranosyl-(1→6)-α-D-glucopyranosyl-(1→4)-α-D-glucopyranosyl-(1→} from α-1,4-glucans, was allowed to act on liquefied starch or partial starch hydrolysate in a high concentration, unexpectedly, enzymatically modified starch was formed by intermolecular and/or intramolecular α-maltosyl-transferring reaction while CMM was formed slightly. The CMM-forming enzyme was disclosed in Japanese Patent Application 174880/2004 (q.v. Japanese Patent Kokai 95148/2005) by the same applicant of the present invention. The studies of the structure and physical properties on the modified starch revealed that a novel branched starch having 6-α-maltosyl and/or 6-α-maltotetraosyl branched structure can be formed by allowing CMM-farming enzyme to act on liquefied starch and partial starch hydrolysate without lowering the molecular weight and increasing the reducing power of the material starchy substance. Further, the present inventors found that the branched starch having 6-α-maltosyl- and/or 6-α-maltotetraosyl-branched structure exhibit marked retrogradation-resistance. The present inventors accomplished the present invention based on the above knowledge.

The present invention attains the above object by providing branched starch having 6-α-maltosyl- and/or 6-α-maltotetraosyl-structure(s) with a marked retrogradation-resistance, a process for producing the branched starch without lowering the molecular weight of material starch, and uses thereof.

According to the present invention, a novel branched starch with a marked retrogradation-resistance can be provided in a large amount and lower cost. The present invention enables the use of the novel branched starch in a various fields including foods and beverages.

Figure 1:
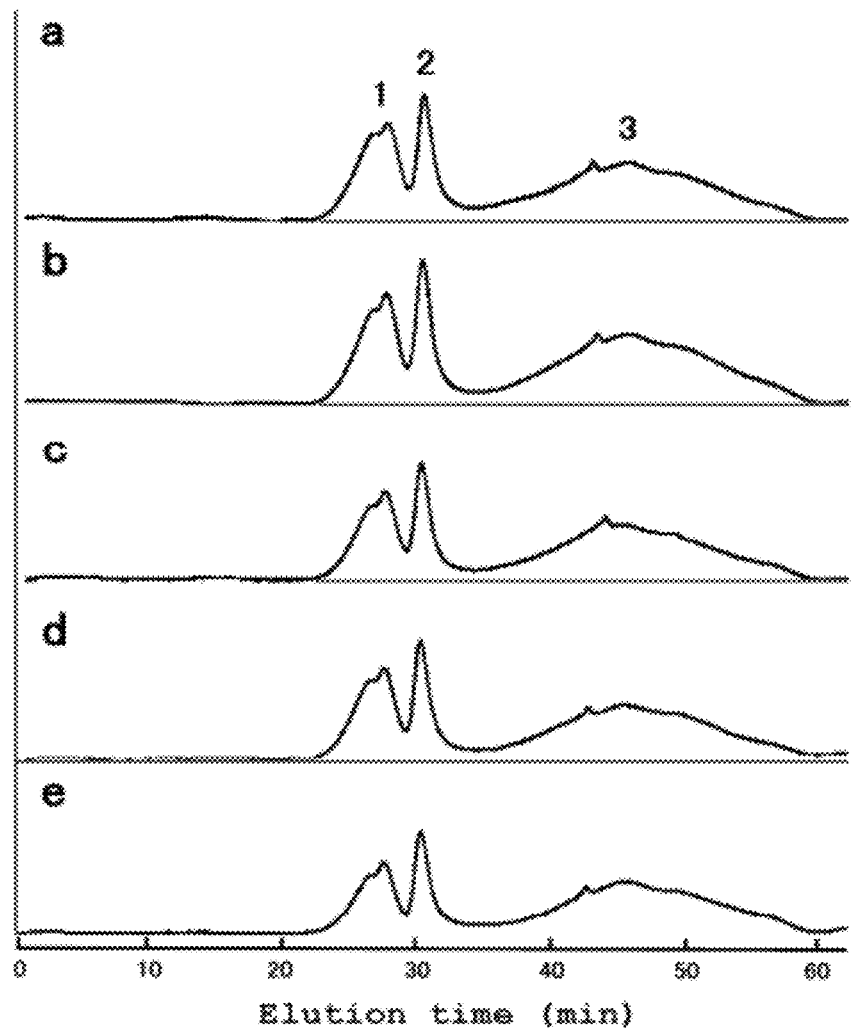
FIG. 1 shows the elution patterns on gel filtration chromatography of some branched starch preparations obtained by allowing CMM-forming enzyme to act on liquefied starch.

EXPLANATION OF SYMBOLS a: Liquefied starch as a control
b: Branched starch preparation No. 1 (prepared using 0.0125 unit of CMM-forming enzyme)
c: Branched starch preparation No. 2 (prepared using 0.025 unit of CMM-forming enzyme)
d: Branched starch preparation No. 3 (prepared using 0.05 unit of CMM-forming enzyme)
e: Branched starch preparation No. 4 (prepared using 0.1 unit of CMM-forming enzyme)
In FIG. 1,
  1: Peak 1 of liquefied waxy corn starch on gel filtration chromatography
  2: Peak 2 of liquefied waxy corn starch on gel filtration chromatography
  3: Peak 3 of liquefied waxy corn starch on gel filtration chromatography
In FIG. 4,
  A: Diagram representing liquefied starch
  B: Diagram representing the branched starch of the present invention
  1: A chain structure where glucoses are bound via α-1,4-glucosidic linkage (Amylose structure)
  2: α-1,6-Branched site of the chain structure
  3: Reducing end glucose
  4: 6-α-Maltosyl-branched structure
  5: 6-α-Maltotetraosyl-branched structure

BEST MODE FOR CARRYING OUT THE INVENTION

Branched starch having 6-α-maltosyl and/or 6-α-maltotetraosyl-branched structure (hereinafter, it may be abbreviate as "branched starch") as referred to as in the present invention means starchy substance, having intramolecularly-branched structure by α-1,6-glucosidic linkage by maltose or maltotetraose unit, including a substance in which maltose or maltotetraose are bound to C-6 position of glucose at a non-reducing end by α-1,6-glucosidic linkage as well as internal glucose of α-1,4-glucan. The molecular weight of the branched starch of the present invention is not restricted, but $1.0 \times 10^4$ daltons or more are preferable. The branched starch having α-6-maltosyl and/or 6-α-maltotetraosyl-branched structure of the present invention is characterized by forming 1.8 w/w % or more of maltose and/or 0.7 w/w % or more of maltotetraose, on a dry solid basis by the action of pullulanase, a starch-debranching enzyme that specifically cleave α-1,6-glucosidic linkage. In comparison to a normal starch with chain length (degree of polymerization) of glucose of mainly 9 to 10, the branched starch of the present invention, which has a branched structure in which chains are very short and have certain length, is distinctly different from the material starch. The branched starch of the present invention has more branching points and shorter chain than normal starch but little decrease of molecular weight.

The fact that branched starch of the present invention having 6-α-maltosyl and/or 6-α-maltotetraosyl branched structure has more branching points than normal starch is revealed by the formation of 2,3,4-trimethyl-1,5,6-triacetylglucitol (hereinafter abbreviated as "2,3,4-trimethylated compound"), indicating the existence of glucose having glucosidic linkage at both C-1 and C-6 positions, at 0.4 w/w % or more of partialy-methylated compounds, on a dry solid basis, which is larger than from the material starch, by a conventional methylation method. It can be revealed also by the smaller β-amylolysis limit than the material starch by a digestion test by β-amylase.

Branched starch of the present invention having 6-α-maltosyl and/or 6-α-maltotetraosyl branched structure have marked retrogradation-resistance compared to the material liquefied starch. As shown in the Experiments described below, an aqueous solution of the branched starch at the concentration of 25% does not become clouded after left at 5° C. for 10 days.

The method using an enzyme forming 6-α-maltosyl and/or 6-α-maltotetraosyl branched structure the material liquefied starch molecule is preferable as a method of preparing branched starch of the present invention having 6-α-maltosyl and/or 6-α-maltotetraosyl branched structure. As the above enzyme, any enzyme which acts on liquefied starch by recognizing maltose structure at a non-reducing end and then transferring the maltose to C-6 position of a glucose at another non-reducing end or an internal glucose of the molecule or C-4 position of a glucose at another non-reducing end by α-maltosyl-transferring reaction. For example, CMM-forming enzyme can be preferably used, which is disclosed in Japanese Patent Application 174880/2004 (q.v. Japanese Patent Kokai 95148/2005) by the same applicant of the present invention.

A CMM-forming enzyme usable for producing a branched starch of the present invention has the mechanism described below.
1) acts on α-1,4-glucans having a glucose polymerization degree of 3 or higher and catalyze the intramolecular 6-α-maltosyl-transferring reaction, by which a maltosyl residue at a non-reducing end is transferred to C-6 position of a glucose residue at a non-reducing end of another α-1,4-glucan molecule to form maltooligosaccharide with glucose polymerization degree increased by 2 having 6-α-maltosyl residue at a non-reducing end and maltooligosaccharide with glucose polymerization degree reduced by 2
2) acts on 6-α-maltosyl-maltooligosaccharide to form CMM having structure of cyclo{→6)-α-D-glucopyranosyl-(1→4)-α-D-glucopyranosyl-(1→6)-α-D-glucopyranosyl-(1→4)-α-D-glucopyranosyl-(1→} by intramolecular α-maltosyltransfering reaction and maltooligosaccharide with glucose polymerization degree reduced by 4 by cyclization.
3) slightly catalyzes intermolecular 4-α-maltosyl-transferring reaction to form maltooligosaccharide with a glucose polymerization degree increased by 2 and maltooligosaccharide with glucose polymerization degree reduced by 2. CMM-forming enzyme of the present invention includes any enzyme catalyzing above reaction regardless of its origin, form, if crude or purified.

As a concrete example of CMM-forming enzyme, the enzyme having the following physicochemical properties can be used.
  (1) Molecular Weight
    72,000±20,000 daltons when determined on SDS-PAGE;
  (2) Isoelectric Point
    pI 3.6±0.5 on isoelectrofocusing using ampholine, a carrier ampholyte;
  (3) Optimum Temperature
    50 to 55° C. when reacted at pH 6.0 for 30 min;
  (4) Optimum pH
    pH 5.5 to 6.5 when reacted at 40° C. for 30 min;
  (5) Thermal Stability
    Stable up to 30° C. when incubated at pH 6.0 for 60 min.
    Stable up to 50° C. in the presence of 1 mM $Ca^{2+}$ ion; and
  (6) pH Stability
    Stable in a pH range of 5.0 to 9.0 when incubated at 4° C. for 24 hours;

Although CMM-forming enzyme of the present invention is not restricted by its source, preferred source is a microorganism, and CMM-forming enzyme from *Arthrobacter globiformis* M6 (FERM BP-8448) can be preferably used. Microorganisms producing CMM-forming enzyme include mutants of the above bacteria as well as the native one and other microorganisms including recombinant and their mutant that can produce CMM-forming enzyme.

CMM-forming enzyme of the present invention used to prepare a branched starch can be used in purified or crude form, or free or immobilized form as long as being feasible for the preparation of the branched starch. When immobilized enzyme is used, the reaction is conducted in any of batch, semicontinuous or continuous method. As method of immobilizing the enzyme, any conventional method is feasible such as carrier binding method (by covalent, ion, or physical binding method), cross-linking method or comprehensive method (lattice or microcapsule type).

As the material starch for preparation of branched starch of the present invention, any of superterranean or subterranean starch is usable, such as corn starch, waxy corn starch, rice starch and glutinous rice starch for example of the former, and such as potato starch, sweet potato starch, tapioca starch and arrowroot starch for example of the latter. For preparing branched starch of the present invention is prepared from the above starch, usually they were advantageously used in gelatinized or liquefied form. As the method of gelatinizing or liquefying, a conventional method can be used.

For example, a method of acting CMM-forming enzyme on a liquefied starch can be conducted as follows. The concentration of the liquefied starch is usually suitable at 10 to 45 w/w %. When the concentration of the liquefied starch is under 10 w/w %, the CMM-forming enzyme easily catalyze intramolecularrmaltosyl transferring reaction and CMM was formed rather than branched starch, resulting in decreased yield of branched starch. When the concentration of the liquefied starch is over 45 w/w %, it is disadvantageous because dissolving the starch in water is difficult.

For the preparation of branched starch of the present invention, CMM-forming enzyme is used at a dose of 0.01 to 10 units, preferably 0.02 to 1 U per 1 g of dry solid of liquefied starch. Activity of one unit of CMM-forming enzyme is defined as the amount of enzyme which forms one µmole of CMM per minute under the condition for measurement of CMM-forming enzyme activity described below. When CMM-forming enzyme is used at under 0.01 units, the reaction proceeds insufficiently with no point in adding the enzyme. When CMM-forming enzyme is used at over 10 units, it is not disadvantageous because of the plateued-effect and higher preparing cost.

The enzyme reaction can be conducted at a temperature of about 60° C. or less, preferably 30 to 50° C. The pH for the reaction is preferable to be controlled at 5 to 9, preferably 5 to 7. The amount of enzyme and reaction time, which are closely related, can be selected according to the desired development of the reaction.

A reaction product of the reaction can be used as the product of branched starch. As appropriate, a solution of an objective branched starch of the present invention can be obtained from the reaction product by centrifugation, elimination of impurity by filtration and condensation of water soluble fraction. The obtained solution of the branched starch can be used as it is, but it is preferable to be a powdery product by drying because of its good storage property and applicability. Dewatering of the product can be conducted by spray-drying method or drum-drying method. Dried product can be ground as appropriate.

A reactant product obtained by allowing CMM-forming enzyme to act on liquefied starch can be used as a branched starch product of the present invention as it is although it contains small amount of CMM. As appropriate, a branched starch purified by elimination of such oligosaccharides can be advantageously used. The purification method can be selected from conventional purification methods for polysaccharide including gel filtration chromatography according to need.

The branched starch of the present invention obtained by above methods is characterized by marked retrogradation-resistance, which is revealed by not becoming clouded after left at a low temperature unlike with normal starch. While ordinary starch is insoluble in cold water, a branched starch of the present invention is soluble in cold water up to the concentration of at least 20 w/w %. The solution of branched starch of the present invention is easy to deal with because of low viscosity compared with the material liquefied starch solution.

The branched starch of the present invention can be used as an alternative for starch in foods or drinks, in which the starch retrogradation is inhibited because of the retrogradation-tolerance of the branched starch. In these foods or drinks, deterioration of water retentivity, shape retentivity, freezing tolerance and digestibility caused by inhibited starch retrogradation. As foods and drinks containing starch, the below ones can be quoted; rice cake, rice dumpling, cookie, bread, noodle, sports drink containing starch and nutritional supplement containing starch.

Branched starch of the present invention can be contained in compositions as described above in the process toward completion by a conventional method such as mixing, kneading, dissolution, soaking, penetration, dispersion, embrocation, coating, spraying, injection and solidification. The amount thereof is preferred to be 1 w/w % or more, preferably 5 w/w % or more, more preferably 10 w/w % or more, according to the purpose.

The branched starch of the present invention possesses characteristics of filling, giving glossy, keeping moisture, viscosity. The branched starch of the present invention is advantageously usable for various compounds such as foods and drinks, articles of taste, feedstuff, bait, cosmetic and medicine, and also for composition for adhering or coating and molded products such as film, sheet, tube, capsule and short bar.

The branched starch of the present invention can be molded in forms, for example, forms of film sheet, tube or capsule with a conventional plastic-molding machine. Molding method is not restricted and any method can be used such as extrusion molding, injection molding, pressure molding, cast molding, stamping molding, cutting molding or film molding method. The obtained molded product is usable as biodegradable plastic. Molded products comprising branched starch of the present invention can contain other water-soluble polysaccharide such as starchy substances including starch, partial starch hydrolysate, amylase, amylopectin, starch derivatives including esterified, etherified, oxidized and/or cross-linked starch, pullulan, sodium arginate, agar, pectin, xanthane gum, dextran, carrageenan, chondroitin sulfate. For control of plasticity of molded products elasticizer can be advantageously added to the molded product. For the elasticizer, water, various kind of polyols such as glycerol, polyalcohols including polyvinylalcohol, sugar alcohols including erythritol, xylitol, sorbitol and maltitol, non-reducing saccharide including $\alpha,\alpha$-trehalose, urea, natural fat and oil including soybean oil and castor oil, and alkylester of organic acid.

Molded product comprising branched starch can also contain inorganic or organic ingredients along with the above ingredients. As an inorganic ingredient, talc, titanium dioxide, calcium carbonate, sand, clay, limestone, diatomite, mica, glass, quartz, ceramics are usable. As an organic ingredient, starch, cellulose, wood dust, fiber, protein and its hydrolysate, fat and lipid, sugar-fatty acid ester, alcohols including ethanol, coloring agent, preservative, flavor and corrigent is usable.

The present invention is concretely explained by the following experiments.

EXPERIMENT 1

Preparation of CMM-forming Enzyme

Prior to the following experiments, CMM-forming enzyme preparation was prepared by culturing *Arthrobacter globiformis* M6, FERM BP-8448, and purifying the resulting enzyme in culture supernatant.

EXPERIMENT 1-1

Cultivation of *Arthrobacter globiformis* M6

A liquid culture medium consisting of 1.5% (w/v) of "Pinedex #4" (a partial starch hydrolysate commercialized by Matsutani Chemical Industries Co., Ltd.), 0.5% (w/v) of "POLYPEPTONE" (a yeast extract commercialized by Nihon Pharmaceutical Co., Ltd.), 0.1% (w/v) of "YEAST EXTRACT S" (a yeast extract commercialized by Nihon Pharmaceutical Co., Ltd.), 0.1% (w/v) of dipotassium phosphate, 0.06% (w/v) of sodium phosphate dehydrate, 0.05% (w/v) of magnesium sulfate hepta-hydrate, 0.3% (w/v) of calcium carbonate, and water was placed in two 500 ml-Erlenmeyer flasks in a respective amount of 100 ml, sterilized by autoclaving at 121° C. for 20 min, and cooled. Successively, the culture medium was inoculated with *Arthrobacter globiformis* M6, FERM BP-8448, and followed the cultivation under rotary-shaking conditions at 27° C. and 230 rpm for 48 hours to prepare a seed culture. About 20 L of a fresh preparation of the same liquid culture medium as used in the above seed culture were placed in a 30-L fermenter, sterilized by heating, and then cooled to 27° C. and inoculated with about 200 ml of the seed culture, followed by the cultivation at 27° C. and pH 5.5 to 8.0 for 96 hours under aeration-agitation conditions. After completion of the cultivation, the resulting culture broth was distilled from the fermenter and removed cells by centrifuging at 8,000 rpm for 20 min, and about 18 L of culture supernatant was obtained.

The enzyme activity of CMM-forming enzyme of the present invention can be assayed as follows: A substrate solution is prepared by dissolving soluble starch in 50 mM acetate buffer (pH 6.0) containing 2 mM $CaCl_2$ to give a concentration of 2% (w/v). A half milliliter of an enzyme solution is added to 0.5 ml of the substrate solution, and the mixture solution is incubated at 40° C. for 30 min. After stopping the reaction by heating at about 100° C. for 10 min, the reaction mixture is admixed with 4,000 units/g-solid of "TRANS-GLUCOSIDASE L AMANO" ($\alpha$-glucosidase commercialized by Amano Enzyme Inc.) and 250 units/g-solid of "GLU-COZYME" (glucoamylase commercialized by Nagase Biochemicals, Ltd.) to hydrolyze remaining soluble starch and by-products, oligosaccharides, and followed by the enzyme treatment at 50° C. for 1 hour. The amount of CMM contained in the treated mixture is determined by high performance liquid chromatography (hereinafter, abbreviated as "HPLC"). One unit activity of CMM-forming enzyme is defined as the amount of enzyme that forms one μmole of CMM per minute under the above conditions. HPLC was carried out under the following conditions:

Column: "Shodex SUGAR KS-801", produced by Showa Denko K. K., Tokyo, Japan

Eluent: Water

Column temperature: 60° C.

Flow rate: 0.5 ml/min

Detector: "RI-8012", a refractive index detector produced by Tosoh Corporation, Tokyo, Japan.

EXPERIMENT 1-2

Purification of CMM-forming Enzyme

About 9.2 L of the culture supernatant was salted out by adding ammonium sulfate to give finally 60% saturation and allowing it to stand at 4° C. for 24 hours. The resultant precipitates were collected by centrifuging at 11,000 rpm for 30 min, dissolved in 10 mM Tris-HCl buffer (pH 7.5), and dialyzed against the same buffer to obtain about 240 ml of a crude enzyme solution. The crude enzyme solution was subjected to anion-exchange column chromatography using 100 ml of "DEAE-TOYOPEARL 650S" gel (an anion-exchange gel commercialized by Tosoh Corporation). CMM-Forming enzyme activity was adsorbed on "DEAE-TOYOPEARL 650S" gel pre-equilibrated with 10 mM Tris-HCl buffer (pH 7.5) and when eluted with a linear gradient increasing from 0 M to 0.4 M of sodium chloride, CMM-forming enzyme activity was eluted at about 0.22 M of sodium chloride. The active fractions were collected and added ammonium sulfate to give a final concentration of 1 M, and then allowed to stand at 4° C. for 24 hours. The enzyme solution was centrifuged to remove precipitates, and subjected to hydrophobic column chromatography using 10 ml of "PHENYL-TOYOPEARL 650M" gel, a gel commercialized by Tosoh Corporation, Tokyo, Japan. CMM-Forming enzyme activity was adsorbed on "PHENYL-TOYOPEARL 650M" gel pre-equilibrated with 20 mM acetate buffer (pH 6.0) containing 1 M of ammonium sulfate and when eluted with a linear gradient decreasing from 1 M to 0 M of ammonium sulfate, CMM-forming enzyme activity was eluted at about 0.1 M of ammonium sulfate. The amount of enzyme activity, specific activity and yield of CMM-forming enzyme in each purification step are in Table 1.

TABLE 1

| Purification step | Enzyme* activity (units) | Specific activity of enzyme* (units/mg-protein) | Yield (%) |
|---|---|---|---|
| Culture supernatant | 240 | 0.13 | 100 |
| Dialyzed solution after salting out with ammonium sulfate | 200 | 0.66 | 83 |
| Eluate from ion-exchange column chromatography | 140 | 7.3 | 58 |
| Eluate from hydrophobic column chromatography | 96 | 10 | 40 |

*CMM-forming enzyme

The purified enzyme preparation of CMM-forming enzyme, obtained by the final hydrophobic column chromatography, was assayed for purify on gel electrophoresis using a 5-20% (w/v) gradient polyacrylamide gel and detected on the gel as a single protein band, i.e. a high purity preparation.

EXPERIMENT 2

Preparation of Branched Starch

The following experiment was performed to investigate the structure and properties of the reaction products formed by allowing CM-forming enzyme to act on the liquefied starch.

EXPERIMENT 2-1

Enzymatic Reaction

Two thousands and five hundreds g of commercially available waxy corn starch (produced by Sanwa Cornstarch Co., Ltd.) was admixed in 25 L of tap water containing 1 mM calcium chloride, then it was adjusted at pH 6.0 with 2 N HCl to give a starch suspension at the concentration of 10 w/w %. The starch suspension was added with 20000 units of "NEOSPITASE K2" (an α-amylase product commercialized by Nagase Biochemicals, Ltd.) and stirred for 30 min, then flowed into a continuously liquefier at a flow rate of 1 L/min. The starch suspension was heated at 100° C. for 25 min and 140° C. for 5 min to give a liquefied starch. The liquefied starch was decolorized with active carbon and filtrated through diatomite, then concentrated up to 25 w/w % under reduced pressure. The concentrated liquefied starch was divided into five equal parts, and four of them were added with 0.0125, 0.025, 0.05, or 0.1 units of purified CMM-forming enzyme preparation per 1 g of dry solid of the liquefied starch followed by incubation at pH 6.0 and 50° C. for 24 hours. The enzyme reaction was stopped by heating at 100° C. for 10 min., the contents of CMM in each reaction solution were determined by HPLC. The material liquefied starch without acting by the CMM-forming enzyme was used as control.

HPLC was carried out under the following conditions:
Column: "MCIgel CK04SS" (produced by Mitsubishi Chemical Corporation) connected in series of two,
Eluent: Water
Column temperature: 80° C.
Flow rate: 0.4 ml/min
Detector: "RI-8012", a refractive index detector produced by Tosoh Corporation.

TABLE 2

| Nos. of Branched starch | Amount* of CMM-forming enzyme | CMM content in the reaction products (%) |
|---|---|---|
| Control | 0 | 0 |
| 1 | 0.0125 | 0.91 |
| 2 | 0.025 | 2.13 |
| 3 | 0.05 | 3.89 |
| 4 | 0.1 | 5.08 |

*Units/g-liquefied starch

As is evident from the results in Table 2, the content of CMM tended to be higher as the added CMM-forming enzyme increased. But even when 0.1 units of the enzyme per 1 g of liquefied starch, which is the maximum amount in this experiment, was used, the content of CMM was small as to be just about 5%.

EXPERIMENT 2-2

Purification of Branched Starch

The reaction solutions obtained in Experiment 2-1 were subjected to filtration, decolorization with active carbon, purification by desalting with H-type and OH type of ion-exchange resin by a conventional way and concentrated with an evaporator up to 20 w/w %. Subsequently, it was fractionated by column using "Amberlite CR-1310, Na-type" (strong acid cation-exchange resin commercially produced by Organo Corporation) to remove CMM as by-product. The resin was packed into four jacketed stainless-steel columns of an inside diameter of 5.4 cm, connected in series to give the resin phase of the total length of 240 cm. Under the conditions of keeping the inner column temperature of 60° C., the starch solution was fed to the column in a volume of 5 v/v % of the resin and fractionated by flowing water of 60° C. at SV 0.13, and the fractions of macromolecule containing no CMM were collected by monitoring the sugar compositions of the eluent with HPLC. The obtained fractions of macromolecule were concentrated up to 25 w/w %, dried in a vacuum and a powdery branched starche were obtained at a yield of 90% or more. These branched starches were analyzed by the same HPLC analysis as Experiment 2-1 and revealed that no CMM was contained.

EXPERIMENT 3

Structural Analyses of Branched Starch

The following experiment was conducted on the branched starch obtained by the method of Experiment 2 to determine the structure of the branched starch.

EXPERIMENT 3-1

Molecular Weight Distribution of Branched Starch

The molecular weight distribution of the branched starch obtained by the method of Experiment 2 was measured by gel-filtration. The gel-filtration analysis was carried out under the following conditions:
Column: "TSK-GEL α-M" (produced by Tosoh Corporation) connected in series of two
Eluent: Water
Column temperature: 30° C.

Flow rate: 0.3 ml/min

Detector: "RI-8012" (a refractive index detector produced by Tosoh Corporation).

The branched starch was suspended in water and added with sodium hydroxide to bring the final concentration of 1 N to dissolve the starch, and after stand at 5° C. overnight, neutralized by 1 N HCl and filtrated through membrane to give the sample for gel-filtration analysis. Liquefied waxy cornstarch solution was analyzed in the same way as control. The molecular weight of the glucan was determined according to the standard curve obtained by the same gel-filtration analysis using standard reference pullulan for molecular weight measurement (commercialized by Hayashibara Biochemical Laboratories, Inc.). The elution patterns of the gel-filtration were shown in FIG. 1. In FIG. 1, "a" indicates the control (the material liquefied starch) and "b", "C", "d" and "e" indicate the branched starch obtained by allowing the CMM-forming enzyme at the dose of 0.0125, 0.025, 0.05 and 0.1 units, respectively, per g of the liquefied starch. Hereinafter, the branched starches obtained by the enzyme dose of 0.0125, 0.025, 0.05 and 0.1 units are referred to "branched starch" No. 1, No. 2, No. 3 and No. 4, respectively.

As evident from the results shown in FIG. 1, three main peaks (indicated as peak 1, 2 and 3 in FIG. 1) are detected on the liquefied starch as control. The weight-average molecular weight of the glucan of the peak 3, which most lately eluted, was determined to be $1.1 \times 10^6$ daltons from the standard curve, but the glucan of peaks 1 and 2, which eluted faster, cannot be determined because they have large molecular weight out of the range of the standard curve. As any of the branched starch No. 1 ("b" in FIG. 1) to 4 ("e" in FIG. 1) showed almost the same elution patterns as the material liquefied starch, it was fount that molecular-weight distributions do not substantially change when subjected to the action of CMM-forming enzyme.

EXPERIMENT 3-2

Hydrolysis Rate of Branched Starch

The reducing powers of the control and the four kind of branched starch obtained in Experiment 2 was measured. The amount of the total sugar and reducing sugar were measured by anthron-sulfuric acid method and by modified Park-Johnson method (Hizukuri et. al., *Carbohydrate research*, Vol. 94, pp. 205-213 (1981)), respectively. The hydrolysis rate, which means the percentage (%) of the amount of reducing sugar to the total sugar, were calculated by the following formula:

Hydrolysis rate(%)=(Amount of reducing sugar)/(Amount of total sugar)×100

TABLE 3

| Nos. of Branched starch | Amount* of CMM-forming enzyme | Hydrolysis rate (%) |
| --- | --- | --- |
| Control | 0 | 0.370 |
| 1 | 0.0125 | 0.366 |
| 2 | 0.025 | 0.405 |
| 3 | 0.05 | 0.439 |
| 4 | 0.1 | 0.482 |

*Units/g-liquefied starch

As is evident from the results in Table 2, on the branched starch prepared at a dose of 0.1 units of CMM-forming enzyme per 1 g of dry solid of liquefied starch, its hydrolysis rate was large by just about 0.1% compared to the liquefied starch as control. It revealed that hydrolysis by the action of CMM-forming enzyme is negligible.

EXPERIMENT 3-3

Methylation Analysis of Branched Starch

The four kinds of branched starch obtained in Experiment 2 and liquefied starch as control were subjected to methylation analysis by a conventional method, to acid hydrolysis, to acetylation. The partially methyl-acetyl-glucitols (hereinafter, may be abbreviated as "partially methylated product") obtained by above method were analyzed by a gas-chromatography method (hereinafter, abbreviated as "GLC") to determine the composition of the partially methylated products. The results were shown in Table 4.

TABLE 4

| | | Composition of partially methylated products* (%) | | | |
| --- | --- | --- | --- | --- | --- |
| Nos. of Branched starch | Amount** of CMM-forming enzyme | 2,3,4-Trimethylated product | 2,3,6-Trimethylated product | 2,3-Dimethylated product | 2,3,4,6-Tetramethylated product |
| Control | 0 | 0.0 | 92.6 | 4.0 | 3.4 |
| 1 | 0.0125 | 0.4 | 91.9 | 3.6 | 4.1 |
| 2 | 0.025 | 1.2 | 90.7 | 4.9 | 3.2 |
| 3 | 0.05 | 4.1 | 86.0 | 6.1 | 3.8 |
| 4 | 0.1 | 4.7 | 85.2 | 5.9 | 4.1 |

*2,3,4-Trimethylated product: 2.3,4-Trimethyl-1,5,6-triacetyl-glucitol 2,3,4-Trimethylated product: 2,3,6-Trimethyl-1,4,5-triacetyl-glucitol 2,3-Dimethylated product: 2,3-Dimethyl-1,4,5,6-tetraacetyl-glucitol 2,3,4,6-Tetramethylated product: 2,3,4,6-Tetramethyl-1,5-diacetyl-glucitol
**Units/g-liquefied starch As is evident from the results in Table 4, it was found that no glucose residue which bind to other glucose at both C-1 and C-6 positions exists in the liquefied starch as control because no 2,3,4-trimethyl product was detected. But 2,3,4-trimethyl product was detected in the branched starch obtained by the action of CMM-forming enzyme. The percentage of the methylated product is higher as the added enzyme increased. This result reveals that the number of the branched structure became larger, in which a C-1 position of a glucose is bound to C-6 position of another glucose, as the enzyme dose increased. In addition, it was found that the number of glucose residue bound to another glucose at C-1, C-4 and C-6 position because the percentage of 2,3-dimethyl product slightly increased. This result indicates that the 6-α-maltosyl transferring reaction catalyzed by the CMM-forming enzyme occurs at C-6 position of glucose residue located internally as well as one at a non-reducing terminal.

EXPERIMENT 3-4

Product from Branched Starch by Pullulanase Digestion

The four branched starch obtained in Experiment 2-2 and the liquefied starch as control were subjected to the action of pullulanase (EC 3.2.1.41), which specifically hydrolyze α-1,6-glucosidic linkage in starch, and the sugar compositions of the pullulanase hydrolysate were measured to determine their branched structure.

The four branched starch obtained in Experiment 2-2 and the liquefied starch as control were dissolved in deionized water at the final concentration of 1 w/v %, added with acetate buffer (pH 6.0) at the final concentration of 20 mM, and added with pullulanase (crystalline product produced by Hayashibara Biochemical Laboratories, Inc.) at a dose of 20 units per 1 g of dry solid of substrate followed by incubation at 40° C. for 2.4 hours. Then heated at 100° C. for 10 min after incubation to inactivate the pullulanase, the sugar composition was measured by the same HPLC analysis in Experiment 2. The results were shown in Table 5. And the results of the liquefied starch as control and the branched starch No. 3 (the dose of CMM-forming enzyme: 0.05 units/g-liquefied starch) were illustrated in FIG. 2, in which the vertical axis means degree of polymerization of glucose and the horizontal axis means the contents (%) of each saccharide in the pullulanase hydrolysate. The symbols "a" and "d" indicates the liquefied starch as control and the branched starch 3, respectively.

TABLE 5

| Nos. of Branched starch | Amount* of CMM-forming enzyme | Composition of maltooligosaccharide having various glucose polymerization degree (DP) in pullulanase hydrolyzate (%) | | | | | | | |
|---|---|---|---|---|---|---|---|---|---|
| | | DP1 | DP2 | DP3 | DP4 | DP5 | DP6 | DP7 | DP8≦ |
| Control | 0 | 0 | 0 | 0 | 0 | 0 | 1.2 | 1.1 | 97.7 |
| 1 | 0.0125 | 0 | 1.8 | 0.5 | 0.7 | 0.7 | 1.4 | 1.4 | 93.5 |
| 2 | 0.025 | 0 | 3.3 | 0.6 | 1.3 | 0.8 | 1.6 | 1.7 | 90.7 |
| 3 | 0.05 | 0 | 3.7 | 0.7 | 2.2 | 1.0 | 1.9 | 2.0 | 88.5 |
| 4 | 0.1 | 0 | 4.8 | 1.5 | 4.1 | 1.8 | 2.9 | 2.8 | 82.1 |

*Units/g-liquefied starch

Figure 2:
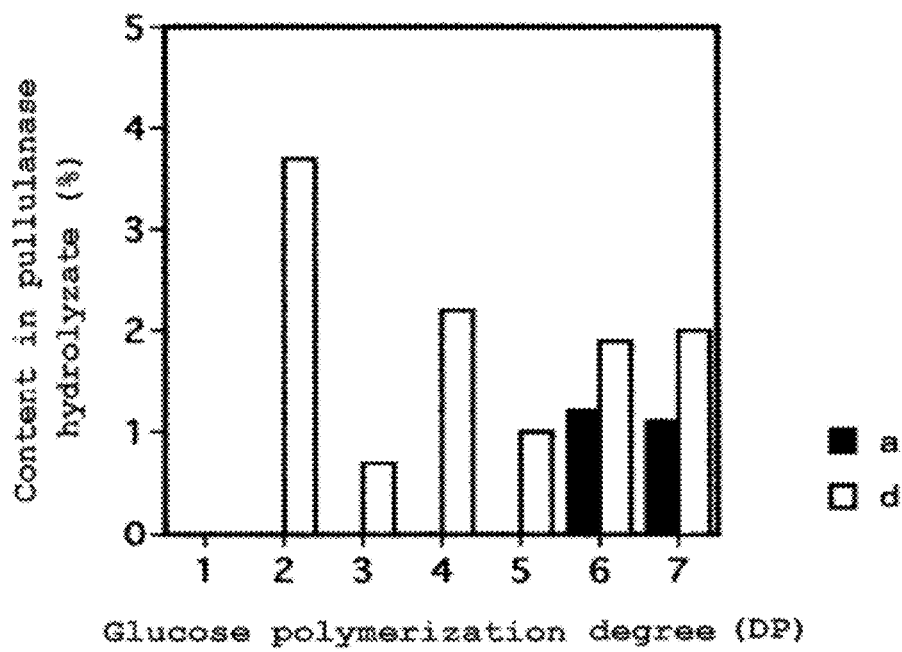
FIG. 2 shows the comparison of the contents of maltooligosaccharides with glucose polymerization degree of 7 or lower in pullulanase hydrolysate of some branched starch preparations obtained by allowing CMM-forming enzyme to act on liquefied starch.

As is evident from the results in Table 5 and FIG. 2, maltooligosaccharides of DP 6 or more but ones of DP 5 or under were formed from the liquefied starch as control, while maltooligosaccharides of DP 5 or less, particularly maltose (DP 2) and maltotetraose (DP 4) were formed much more from the branched starch obtained by the action of CMM-forming enzyme. These results revealed that novel branched starch having 6-α-maltosyl and/or 6-α-maltotetraosyl branched structure was formed by the action of the CMM-forming enzyme.

EXPERIMENT 3-5

β-Amylolysis of Branched Starch (Limit of β-amylase Digestion)

The solutions of four branched starch obtained in Experiment 2-2 and the liquefied starch as control were prepared at the final concentration of 1 w/v % with 20 mM of acetate buffer (pH 6.0). The solutions were added with β-amylase (soybean-derived product by Nagase Biochemicals, Ltd.) at a dose of 100 units per 1 g of dry solid, incubated at 50° C. for 24 hours and then the enzyme reactions were terminated by heating at 100° C. for 10 min. One unit of β-amylase activity was defined as the amount of the enzyme producing the reducing power corresponds to 1 μmole of maltose in 1 minute from the 1 w/w % of soluble starch at pH 5.5 and 40° C. The contents of maltose and β-limit dextrin, which is not further hydrolyzed by β-amylase, in the β-amylase hydrolysate were measured by the same HPLC condition as in Experiment 1. The results were shown in Table 6.

TABLE 6

| Nos. of Branched starch | Amount* of CMM-forming enzyme | Saccharide composition (%) | |
|---|---|---|---|
| | | Maltose | β-Limit dextrin |
| Control | 0 | 56.1 | 43.9 |
| 1 | 0.0125 | 41.8 | 58.2 |
| 2 | 0.025 | 35.1 | 64.9 |
| 3 | 0.05 | 29.4 | 70.6 |
| 4 | 0.1 | 22.9 | 77.1 |

*Units/g-liquefied starch

As is evident from the results in Table 6, the contents of maltose formed by β-amylolysis from the branched starch were larger and the contents of β-limit-dextrin were smaller as the dose of CMM-forming enzyme was increased. As β-amylase hydrolyze starch from the non-reducing ends by maltose unit and the hydrolysis is stopped just before the branched structure of α-1,6-glucosidic linage, the above results revealed that the branched structures were formed by α-1,6-transmaltosylation by the action of CMM-forming enzyme and the content of the branched structure become larger as the dose of CMM-forming enzyme increased.

EXPERIMENT 3-6

Iodine Stain of Branched Starch

Figure 3:
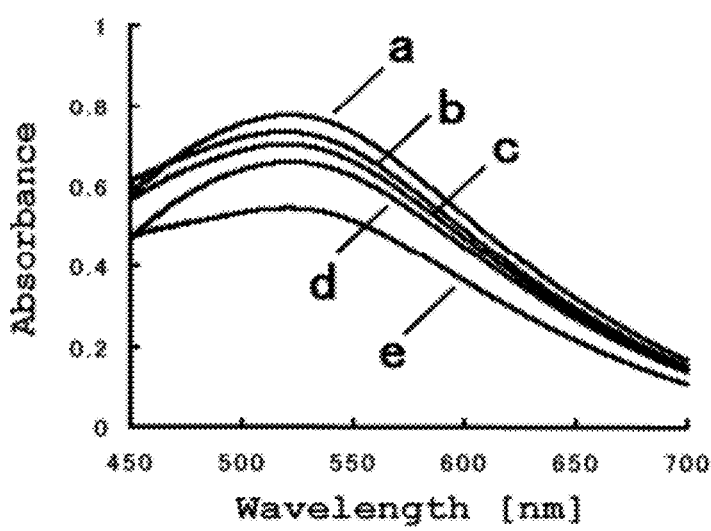
FIG. 3 shows the adsorption spectra of starch-iodine complexes prepared using some branched starch preparations obtained by allowing CMM-forming enzyme to act on liquefied starch.

The four branched starch obtained in Experiment 2-2 and the liquefied starch as control were dissolved in deionized water at the concentration of 0.15 w/w % and 0.5 ml of the solutions were added with 10 ml of 0.02 N sulfuric acid and 0.1 N iodide-potassium solution. After standing at 25° C. for 25 min, the absorption spectra of the iodine-starch complex were measured in a range of wavelength of 450 to 700 nm. The results were shown in FIG. 3. The symbols "a", "b", "c", "d" and "e" means the same as in FIG. 1 of Experiment 3-1. As is evident from the results shown in FIG. 3, the absorbance was lower as the dose of CMM-forming enzyme increased. The wavelength of the maximum absorbance was 520 nm, which was almost the same among the samples. It was considered from the results in Experiment 3-2 that the absorbance was lower as the dose of CMM-forming enzyme increased even though hydrolyzed little by CMM-forming enzyme, because the abundance of the straight-chain structure in which the iodide-complex was formed in starch was lower as the dose of CMM-forming enzyme increased, resulting in lowering the amount of iodide absorbed to the starch.

Figure 4:
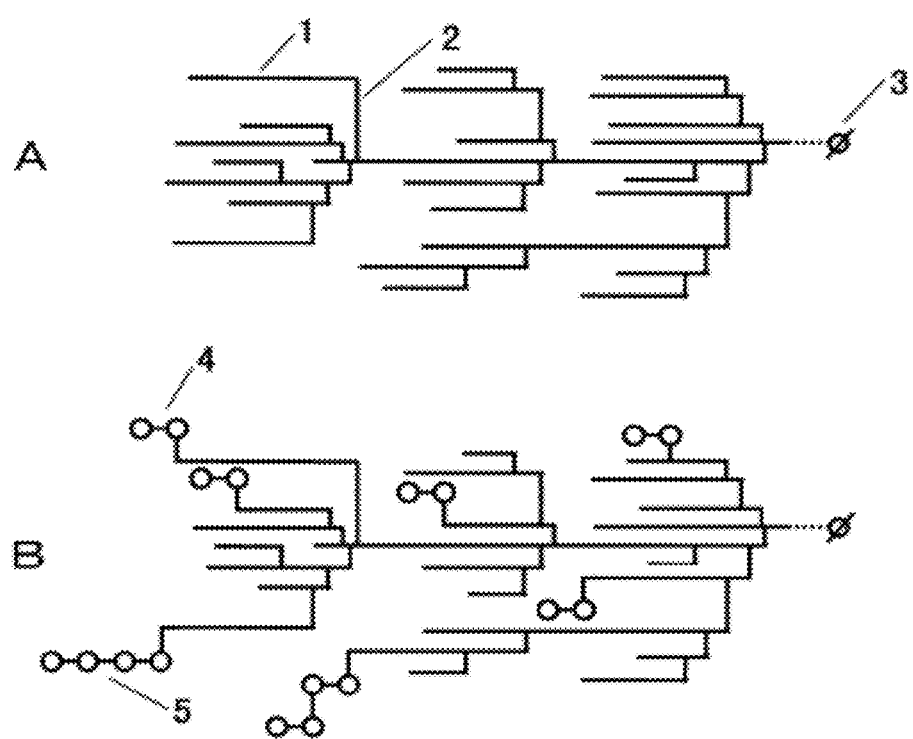
FIG. 4 shows the diagrams representing the structures of material liquefied starch and the branched starch of the present invention.

From the results in Experiment 3, it was found that the branched starch obtained from the liquefied starch by the action of CMM-forming enzyme was the novel branched starch having 6-α-maltosyl and/or 6-α-maltotetraosyl branched structure. FIG. 4 shows diagrams of the structure of the branched starch of the present invention and liquefied starch, in which A means the latter and B means the former. In FIG. 4, No. 1, No. 2 and No. 3 means a straight-chain structure of glucose polymerized by α-1,4-glucosidic linkage (structure of amylase), a position at which above structure branched by α-1,6-glucosidic linkage and the glucose residue at the reducing end, respectively. And the No. 4 and No. 5 means 6-α-maltosyl and 6-α-maltotetraosyl branched structure in the branched starch of the present invention.

EXPERIMENT 4

Retrogradation-resistant Property of Branched Starch

Figure 5:
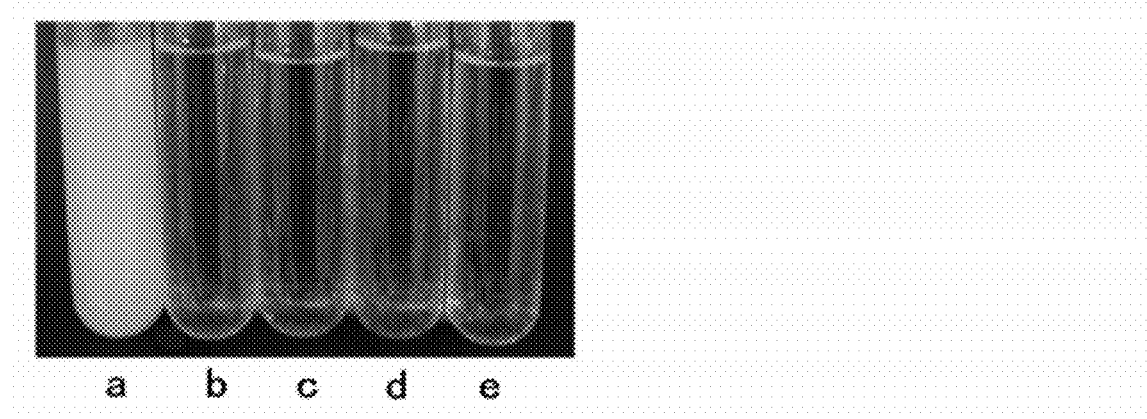
FIG. 5 shows the photograph comparing the branched starch of the present invention and material liquefied starch after the steps of dispensing 25% (w/w) of these aqueous solutions into respective glass tube and preserving them in a refrigerator at 5° C. for 10 days.

The retrogradation-resistance was investigated on four branched starches obtained in Experiment 2 and the liquefied starch as control. Each sample was dissolved in water by heating to bring the concentration of 25 w/w %, and the solutions were dispensed into glass test tube, then the degree of retrogradation was observed after stand at 5° C. for 10 days. The results were shown in FIG. 5. The symbols of "a", "b", "c", "d" and "e" means the same as in Experiment 3-1 and FIG. 1. As is evident from the results in FIG. 5, the liquefied starch as control (a) highly retrograded as to be clouded and partially solidified at the above condition. Meanwhile, it was found that the branched starches (b-e) obtained by the action of CMM-forming enzyme, which have 6-α-maltosyl and 6-α-maltotetraosyl branched structure, were markedly retrogradation-resistant because they remained to be transparent liquid.

The following examples further explain the present invention specifically. Examples of the process for producing the branched starch of the present invention are in Examples 1 to 5, and compositions comprising the branched starch of the present invention in Examples 6 to 14. However, they do not restrict the present invention.

EXAMPLE 1

Waxy-corn starch (produced by Sanwa Cornstarch Co., Ltd.) was suspended in tap water, added with calcium chloride at the concentration of 1 mM and adjusted at pH 6.0 to give a starch suspension at the concentration of about 10%. The suspension was added with "SPITASE HS" (thermostable α-amylase produced by Nagase Biochemicals, Ltd.) at the dose of 0.05 mg per 1 g of dry solid of starch, stirred for 30 min and flowed into a continuously liquefier at a flow rate of 1 L/min. The starch suspension was heated at 100° C. for 25 min and 140° C. for 5 min to give a liquefied starch. The liquefied starch solution was concentrated up to about 25 w/w %, added with CMM-forming enzyme at the dose of 0.1 units per 1 g of dry solid of starch and reacted at pH 6.0 and 50° C. for 20 hours. After the enzyme reaction was terminated by heating at 100° C. for 20 min, the reaction solution was cooled and subjected to filtration, decolorization with active carbon and diatomite-filtration by a conventional method to give the branched starch solution at the concentration of about 25 w/w %, at the yield of about 90%, on a dry solid basis. The pullulanase hydrolysate of the obtained branched starch contained 3.7 w/w % of maltose and 1.7 w/w % of maltotetraose. The partially methylated products of the branched starch contained 8.2 w/w % of 2,3,4-trimethylated product. The branched starch product contained 96.7 w/w of branched starch and 3.3 w/w % of CMM. The branched starch product is usable for many kinds of compositions such as foods and drinks, cosmetics and medicines as taste-improving agent, conditioning agent, water-separation-preventing agent, stabilizer, discoloration-preventing agent, fillers, clathrator, powdering-carrier because of its adequate viscosity, moisture-keeping property, retorgradation-resistance and clathrating property.

EXAMPLE 2

The solution of the branched starch obtained in Example 1 was subjected to decolorization with active carbon, purification by desalting with H-type and OH-type ion-exchange resin by a conventional way and concentrated with a evaporator up to 20 w/w %, on a dry solid basis. Then, it was applied to column fractionation using "Amberlite CR-1310, Na-type" (an strong acid cation-exchange resin produced by Organo Corporation) to remove CMM as a by-product. The resin was packed into four jacketed stainless-steel columns of the inside diameter of 5.4 cm and they were connected in series to give the resin phase of the total length of 240 cm. Under the conditions of keeping the inner column temperature of 60° C., the starch solution was fed to the column in a volume of 5 v/v % of the resin and fractionated by flowing water of 60° C. at SV 0.13. The fractions of macromolecule containing no CMM were collected, concentrated up to 25 w/w % and powderized by dewatering and drying with "PULCO" (a pulse dewatering system produced by PULTEC Corporation). The powdery branched starch obtained by this method possessed low hygroscopicity and good granularity. This product possessed good water-solubility as to be dissolved in water up to the concentration of 30 w/w %. This product is usable for many kinds of compositions such as foods and drinks, cosmetics and medicines as taste-improving agent, conditioning agent, water-separation-preventing agent, stabilizer, discoloration-preventing agent, fillers, clathrator, powdering-carrier because of its adequate viscosity, moisture-keeping property, retorgradation-resistance and clathrating property.

EXAMPLE 3

"Pinedex #100" (a commercial partially-hydrolyzed starch produced by Matsutani Chemical Industries Co., Ltd.) was dissolved in water to give the concentration of about 30 w/w %, added with calcium chloride to bring the final concentration of 1 mM and adjusted at pH 6.0. The solution was added with CMM-forming enzyme obtained by the method of Experience 1 at a dose of 1 unit per g of dry solid of the substrate, reacted at 40° C. for 48 hours, and then the reaction was stopped by heating at 100° C. for 10 min. The reaction solution was purified by decolorization with active carbon and diatomite-filtration by a conventional method and concentrated up to 30 w/w % to give a branched partial starch hydrolysate solution at the yield of about 90 w/w %, on a dry solid basis. This product contained 90.8 w/w % of branched partial starch hydrolysate with glucose polymerization degree of 7 or more, 6.7 w/w % of maltooligosaccharides with glucose polymerization degree of 1 to 6 and 2.5 w/w % of CMM, on a dry solid basis. This product is usable for many kinds of compositions such as foods and drinks, cosmetics and medicines as taste-improving agent, conditioning agent, water-separation-preventing agent, stabilizer, discoloration-preventing agent, fillers, clathrator, powdering-carrier because of its adequate viscosity, moisture-keeping property, retorgradation-tolerance and clathrating property.

EXAMPLE 4

A branched partial starch hydrolysate solution was obtained by the same way of Example 3 except for allowed isoamylase to act at a dose of 2500 units per g of dry solid of the substrate. It was purified by decolorization with active carbon and diatomite-filtration by a conventional method and concentrated up to 30 w/w % at the yield of about 90%, on a dry solid basis. This product contained 69.6 w/w % of branched partial starch hydrolysate with glucose polymerization degree of 7 or more, 27.3 w/w % of maltooligosaccharides with glucose polymerization degree of 1 to 6 and 3.1 w/w % of CMM, on a dry solid basis. This product is usable for many kinds of compositions such as foods and drinks, cosmetics and medicines as taste-improving agent, conditioning agent, water-separation-preventing agent, stabilizer, discoloration-preventing agent, fillers, clathrator, powdering-carrier because of its adequate viscosity, moisture-keeping property, retrogradation-tolerance and clathrating property.

The pullulanase hydrolysate of this product was a transparent solution containing 41.5 w/w % of maltose and 26.2 w/w % of maltotetraose. The content of maltose and maltotetraose of this product was 1.5-fold compared to the branched partial starch hydrolysate obtained in Example 3. These results revealed that the number of 6-α-maltosyl and/or 6-α-maltotriosyl branched structure is increased by the action of CMM-forming enzyme along with the cleavage of branched points of branches with high glucose polymerization degree by isoamylase.

EXAMPLE 5

The branched partial starch hydrolysate solution obtained in Example 4 was subjected to filtration, decolorization with active carbon and purification by desalting with H-type and OH-type ion-exchange resin by a conventional method and concentrated up to 20 w/w %. Then, it was subjected to column fractionation using "Amberlite CR-1310, Na-type" (an strong acid cation-exchange resin produced by Organo Corporation) to remove oligosaccharides as by-products including CMM. For the fractionation, the resin was packed in four jacketed stainless-steel columns of the inside diameter of 5.4 cm and they were connected in series to give the resin phase of the total length of 240 cm. The starch solution was fed to the column under conditions of keeping the inner column temperature at 60° C. in a volume of 5 v/v % of the resin and fractionated by flowing water of 60° C. at SV 0.13. The fractions of macromolecule containing no oligosaccharide were collected, concentrated up to 25 w/w % and powderized by dewatering and drying with "PULCO" (a pulse dewatering system produced by PULTEC Corporation). The powdery branched starch obtained by this method possessed low hygroscopicity and good granularity. This product possessed good water-solubility as to be dissolved in water up to the concentration of 30 w/w %. This product is usable for many kinds of compositions such as foods and drinks, cosmetics andmedicines as taste-improving agent, conditioning agent, water-separation-preventing agent, stabilizer, discoloration-preventing agent, fillers, clathrator, powdering-carrier because of its adequate viscosity, moisture-keeping property, retrogradation-tolerance and clathrating property.

EXAMPLE 6

"Ohagi" (Rice Dumpling Covered with Bean Jam)

Three hundreds and fifty parts by weight of "SUN-MALT®" (a maltose product commercialized by Hayashibara Shoji Inc.) and 150 parts by weight of "TREHA®" (a trehalose product commercialized by Hayashibara Shoji Inc.) were dissolved in hot water to give the solution of the concentration of 70 w/w % and kept at 55° C. Eight hundreds parts by weight of glutinous rice preliminarily soaked in water was steamed in steam cooker, cooled up to 55° C. and homogeneously admixed with 500 parts by weight of the above saccharide solution and 200 parts by weight of the branched starch obtained by the method of Example 3. After kept in a keep-warm vessel at 45-55° C. for 1 hour, it was shaped into "ohagi" using puréed bean jam. The quality of the "ohagi" is high as to get into little water-separation after thawing followed by freezing or refrigerating storage and keep softness as just prepared because it contained the retrogradation-resistant branched starch.

EXAMPLE 7

"Uiro" (Sweetened Rice Paste)

Seventy parts by weight of rice flour was homogeneously admixed with 40 parts by weight of branched starch obtained by the method of Example 2, 70 parts by weight of anhydrous crystalline maltitol, 50 parts by weight of "TREHA®" (a trehalose product commercialized by Hayashibara Shoji Inc.) and 4 parts by weight of pullulan to give a base of "uiro". The base of "uiro", ground tea and water were kneaded and steamed in a case for 60 min to give a ground-tea-taste "uiro". This product possesses good gloss, taste and flavor. It can be kept for a long time because of inhibited starch-retrogradation and used as low-calorie "uiro".

EXAMPLE 8

Custard Cream

One hundred parts by weight of branched starch, obtained by the method in Example 2,100 parts by weight of "TETRUP®" (a syrup comprising maltotetraose commercialized by Hayashibara Shoji Inc.), 60 parts by weight of hydrous crystalline trehalose, 40 parts by weight of sucrose, and one part by weight of sodium chloride were mixed well, and then 280 parts by weight of whole egg was further admixed with the mixture. Successively, 1,000 parts by weight of boiled milk was gradually admixed with the resulting mixture and the resulting solution was continuously stirred on an open flame. The heating was stopped at the point that the mixture gave a transparency. After cooling the mixture, a suitable amount of vanilla essence was admixed with the mixture. The resulting mixture was weighted, filled, and packed to make into a product. The product is a high quality custard cream with a satisfactory gloss and flavor, whose retrogradation of starch is inhibited.

EXAMPLE 9

Powdery Peptide Product

To one part by weight of "HI-NUTES" (40% soybean peptides solution for foods, commercialized by Fuji Oil Co., Ltd.) and two parts by weight of branched starch obtained by the method in Example 2 was mixed and the resulting mixture was put into a plastic tray, dried at 50° C. under a reduced pressure, and pulverized to make into a powdery peptide product. The product has a satisfactory flavor and is useful as a material for premix, low-calorie confectionaries for ice dessert. Further, the product is useful as a material for a fluid diet for oral- or tube-intake.

EXAMPLE 10

Solid Agent for a Fluid Diet

One hundred parts by weight of a powdery branched starch, obtained by the method in Example 2, 200 parts by weight of hydrous crystalline trehalose, 200 parts by weight of a maltotetraose high content powder, 270 parts by weight of powdery egg yolk, 209 parts by weight of skim milk, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 parts by weight of vitamin E acetate, and 0.04 part by weight of nicotinic acid-amide were mixed to make into a composition. Twenty-five grams each of the composition was packed into a dampproof laminate pouch, and the pouch was heat-sealed to make into a product. Since the product comprises branched starch with a retrogradation-resistant property, it can be advantageously used for supplying energy to living bodies as a fluid diet to regulate the function of intestine by taking orally or through tube into nasal cavity, stomach, and intestine.

EXAMPLE 11

Tablet

Fifty parts by weight of aspirin, 14 parts by weight of a powdery hydrous crystalline trehalose and 4 parts by weight of the branched starch obtained by the method in Example 3 were mixed well. Then, according to a conventional method, the mixture was shaped into a tablet with a sickness of 5.25 mm and 680 mg/tablet using a tablet machine. The product was prepared by applying the shaping ability of trehalose and branched starch. The product shows no hygroscopicity and has a satisfactory physical strength and water-decaying property.

EXAMPLE 12

Ointment for Curing Wound

Four hundred parts by weight of maltose was admixed with 50 parts by weight of a methanol solution containing three parts by weight of iodine were mixed, then admixed with 200 parts by weight of the solution of 10 w/w a of the powdery products containing branched starch to give a ointment for curing wound with an adequate extendability and adhesive property. Since it possesses adequate viscosity and moisturizing property by the branched starch, the product is an ointment with a high marketability and less change over time. Since iodine in the product has an antimicrobial activity and maltose in the product acts as an energy-supplement for cells, the curing period is shortened and wound surface is cured completely.

EXAMPLE 13

Films

The branched starch solution obtained by the method of Example 1 was adjusted at the concentration of 25 w/w %. A few drops of the solution were dropped on a polyethylene terephthalate film fixed on a flat plate, spread with "bakery-applicator Model: YBA" (an applicator produced by Yoshimitsu Seiki K. K.), dried at a room temperature for 4 hours to give a film with a thickness of 9 μm and a moisture-content of 10.5 w/w %. The dried film of the branched starch was exfoliated from the polyethylene terephthalate film, stored in a desiccator conditioned at a humidity of RH 52.8% overnight to give a product. This product was a good-quality film possessing high clarity, gloss and flexibility. The film possessed the tensile strength of 1.760 kgf and good water-solubility. The film is usable as an edible film.

EXAMPLE 14

Films

Eight parts by weight of the branched starch obtained by the method of Example 2, 2 parts by weight of "NEWGELIN NC-400" (a carrageenan commercialized by Chuo Foods Material Co., Ltd.) 0.01 parts by weight of "SUGARESTER S1670" (a sucrose-stearate ester commercialized by Mitsubishi-Kagaku Foods Corporation), 25 parts by weight of glycerol and 65 parts by weight of deionized water were mixed and dissolved by heating. Adequate amount of the solution was dropped onto a polyethylene terephthalate film fixed on a flat glass plate, spread with "bakery-applicator Model: YEA" (an applicator produced by Yoshimitsu Seiki K. K.), gelated and dried at 50° C. for 6 hours to give a branched-starch film with a thickness of 0.5 mm and a moisture-content of about 18%. The film possessed good heat-sealability, clarity, breakability and water-solubility to be usable for an edible film and capsule.

EXAMPLE 15

Capsules

Two hundreds and fifty parts by weight of the branched starch obtained by the method of Example 2, 20 parts by weight of "NEWGELIN NC-400" (a carrageenan commercialized by Chuo Foods Material Co., Ltd.), 40 parts by weight of glycerol and 700 parts by weight of deionized water were mixed and dissolved by heating to give a material solution, then defoamed under reduced pressure. The solution was kept at 50° C. and the tips of the capsule-forming pins were dipped in the solution, pulled out and dried to give hard-capsules. The capsule possessed the glossy surface, good clarity, and no oxygen-perviousness and good humidity stability. The capsule can be used as a container of foods or medicines because of its slow breakability in water solution.

EXAMPLE 16

Capsules

Two hundreds parts by weight of "PULLULAN PF-20" (a pullulan product commercialized by Hayashibara Shoji Inc.), 50 parts by weight of the branched starch obtained by the method of Example 5, 1 part by weight of "NEWGELIN NC-400" (a carrageenan commercialized by Chuo Foods Material Co., Ltd.), 2 parts by weight of ammonium chloride and 750 parts by weight of water were mixed and dissolved by heating to give a material solution, then defoamed under reduced pressure. The solution was kept at 50° C. and the tips of the capsule-forming pins were dipped in the solution, pulled out and dried to give hard-capsules. The capsule possessed the glossy surface, good clarity, and no oxygen-perviousness and good humidity stability. The capsule can be used as a container of foods or medicines because of its slow breakability in water solution.

EXAMPLE 17

Fertilizer in Pile Shape

Seventy parts by weight of mixed fertilizer (N=14%, $P_2O_5$=8%, $K_2O$=12%), 10 parts by weight of the branched starch by the method of Example 2, 15 parts by weight of calcium sulfate and 5 parts by weight of water were sufficiently mixed and shaped by a extruder (L/D=20, compression ratio=1.8, the diameter of the die=30 mm) by heating at 80° C. to give a fertilizer in pile shape. The product is so easy to be used that a fertilizer-container is unnecessary. The product possesses adequate strength for thick application and the releasing rate of the ingredients can be regulated by altering the compounding ratio. If necessary, a phytohormone, an agricultural agent, and a soil-improving agent can be easily mixed in the fertilizer in pile shape.

INDUSTRIAL APPLICABILITY

According to the present invention, liquefied starch can be changed in the properties without little decrease of its molecular weight and a novel branched starch having densely-branched structure and retrogradation-resistance can be provided in large amounts and low cost. The novel branched starch of the present invention is usable for starch-rich sports drink or nutritional supplement by its high solubility. The branched starch can be used as a replacement starch for foods containing starch to inhibit various deterioration caused by the starch-retrogradation. The branched starch is expected to be useful not only for foods but also for industrial application such as materials for adhesive agent or biodegradable plastics and for medical application such as materials of films including oblate and capsules. The present invention is significantly important by greatly contributions to many industrial fields.

The invention claimed is:

1. A process for producing a modified branched starch, which comprises the steps of:
    (a) allowing β-amylase to act on a branched starch, having a 6-α-maltosyl- and/or 6-α-maltotetraosyl-branched structures at the non-reducing ends of said branched starch, to hydrolyze said branched starch from its non-reducing ends by maltose unit to form a modified branched starch containing maltose; and
    (b) collecting the formed modified branched starch.

2. The process of claim 1, wherein the branched starch on which β-amylase is allowed to act forms 0.4% (w/w) or higher, on a dry solid basis, of 2,3,4-trimethyl-1,5,6-triacetyl-glucitol as a partially methylated compound when the branched starch is subjected to methylation analysis.

* * * * *